United States Patent [19]

Seamark et al.

[11] Patent Number: 5,573,933
[45] Date of Patent: Nov. 12, 1996

[54] TRANSGENIC PIGS

[75] Inventors: Robert F. Seamark; Julian R. E. Wells, both of Adelaide, Australia

[73] Assignee: Luminis Pty, Ltd., Australia

[21] Appl. No.: 226,408

[22] Filed: Apr. 12, 1994

Related U.S. Application Data

[63] Continuation of Ser. No. 808,194, Dec. 13, 1991, abandoned, which is a continuation-in-part of Ser. No. 294,562, filed as PCT/AU88/00109, Apr. 14, 1988, abandoned.

[30] Foreign Application Priority Data

Apr. 14, 1987 [AU] Australia ................................. PI1427
Nov. 10, 1987 [AU] Australia ................................. PI5326

[51] Int. Cl.$^6$ .................................................. C12N 15/00
[52] U.S. Cl. .................... 435/172.3; 435/320.1; 435/69.4; 800/2; 800/DIG. 1; 935/13
[58] Field of Search .............................. 435/172.3, 69.4, 435/320.1; 800/2,DIG. 1; 935/13

[56] References Cited

U.S. PATENT DOCUMENTS 4,873,191  10/1989  Wagner et al. ....................... 435/172.3

FOREIGN PATENT DOCUMENTS

| | | |
|---|---|---|
| 2092983 | 3/1983 | Australia . |
| 1933183 | 9/1983 | Australia . |
| 0177343 | 4/1986 | European Pat. Off. . |
| 8204443 | 12/1982 | WIPO . |

OTHER PUBLICATIONS

J. Brosius et al., "Gene Organization and Primary Structure of a Ribosomal RNA Operon from *Escherichia Coli*", *J. Mol. Biol.*, 148(2):107–127 (May 1981).

J. Brosius et al., "Spacing of the —10 and —35 Regions in the Tac Promoter", *J. Biol. Chem.*, 260(6):3539–3541 (Mar. 1985).

H. A. de Boer et al., "The tac promoter: A functional hybrid derived from the trp and lac promoters", PNAS–USA, 80:21–25 (Jan. 1983).

F. M. DeNoto et al., "Human Growth Hormone DNA Sequence and mRNA Sequence: Possible Alternative Splicing", *Nucl. Acids Res.*, 9:3719–3730 (1981).

Hsiung et al. (Becker and Hsiung), "Expression, Secretion and Folding of Human Growth Hormone in *Escherichia coli*", *Febs. Letters*, 204(1):149–150 (1986).

Robins, personal communication, (1990).

Kadonaga et al., "Promoter–specific Activation of RNA Polymerase II Transcription of Spl", *Trends in Biochem. Sci.*, 11:20–23 (1986).

Nonander et al., "Construction of Improved M13 Vectors Using Oligodeoxynucleotide–Directed Mutagenesis", *Gene*, 26:101–106 (1981).

Seeburg et al., "Efficient Bacterial Expression of Bovine and Porcine Growth Hormones", DNA 2:37–45 (1983).

Tranplantation of the Human Insulin Gene into Fertilized Mouse Eggs.

Metallothionein–Human GH Fusion Genes Stimulate Growth of Mice.

Dramatic Growth of Mice that Develop from Eggs Microinjected with Metallothionein–Growth Hormone Fusion Genes.

Developmental Fate of a Human Insulin Gene in Transgenic Mouse.

Production of Transgenic Rabbits, Sheep and Pigs by Microinjection.

Isolation and Characterization of the Porcine Growth Hormone Gene.

Development of 1–Cell and 2–Cell Pig Ova After Microinjection of Genes.

Van Brant, Biotechnology 6(10):1147, 1151, 1152, 1154 (1988).

Karin et al., Nature 299:797–802 (1982).

*Primary Examiner*—Jasemine C. Chambers
*Attorney, Agent, or Firm*—Merchant, Gould, Smith, Edell, Welter & Schmidt, P.A.

[57] ABSTRACT

A method for preparing transgenic pigs is disclosed. The method comprises the steps of: obtaining a recently fertilized pig ovum; isolating a first DNA sequence encoding a suitable promoter region; inserting the first DNA sequence into a plasmid cloning vector; isolating a second DNA sequence encoding a porcine growth hormone gene; inserting the second DNA sequence into the plasmid cloning vector; introducing the plasmid cloning vector into the male pronucleus; and, subsequently implanting the ovum into a female pig.

14 Claims, 13 Drawing Sheets

Fig. 3a.

```
CCCGCGGGACATGACCCAGAGGAGCACCCGGAACAGGATCAGTCGGAGCAGTTCTAAATATCCATTAGCACATCCCTCCCAGTGGGCATGCATAAATGTATAG
                    -150                                      -100
AGAAATAGGTGGGGCAGAGGACAGAGAAGAGGCCAGGG TATAAAA AGCCCCAAAGGGACCAATCC A GAATCCAGGACCACCAGCTCCCAGACCACTC
                    -50                          met ala ala g    +1
AGGGACCTGTGGACAGCTCACCGGCTGTG ATG GCT GCA G GCAAGTGCCCCTAAAATCCCAGTGCCTTGGTCTGTTCTCAAGGGTGACGTGGGCCATCCAG
                    +50                                                    +100
ATGGATGGGGCACCAACCTTGGGGTTTCCGAATGTGAGCATGGATATCTACTCCTAGATATGAGGCCAAGTTTAAATGTCCCTGGGGGAGGGGAGGAG
                    +150                                      +200
                                                                         ly pro arg thr ser ala leu leu ala
AACGGCACAGCCTGGTGCAGCCAGGCCCTCTTGTCTCTGGATCCCTCTCACGGCCCCTCCTCTGGTCTCTAG GC CCT CGG ACC TCC GCG CTC CTG GCT
                    +250                                      +300                                    I*
phe ala leu leu cys leu pro trp thr arg glu val gly ala phe pro ala met pro leu ser ser leu phe ala asn ala
TTC GCC CTG CTC TGC CTG CCC TGG ACT CGG GAG GTG GGC GCC TTC CCA GCC ATG CCC TTG TCC AGC CTA TTT GCC AAC GCC
                    +350           A*                           +400
val leu arg ala gln his leu his gln leu ala ala asp thr tyr lys glu phe
GTC CTC CGG GCC CAG CAC CAG CAC CTG GCT GCT GAC ACC TAC AAG GAG TTT GTAAGCTCCCCAGGGGAGGGTGCTGGAGGGGGTGG
                    +450         C                                           +500
TGGAGAGGGTGAATTCGTCCCTCTCTGCCTAGTGGCAGGAAAATGAGGGTTCTGGAGTATTCAGGCCAACCGAAGATGCTATCAGGTGAGTGTAAACTGAAGGGG
                    +550                                      +600
```

Fig. 3b.

```
                                                            glu arg ala tyr ile pro glu gly gln
                                                            GAG CGC GCC TAC ATC CCG GAG GGA CAG
ATTCCCAAGAAAGCAGCAAGGAGAACCGGCCCCACTGTAGACCTGATGGTCTCCCTCTCCCAG
                              +650                                              +700 arg tyr ser ile gln asn ala ala phe cys phe ser glu thr ile pro ala pro thr gly lys asp glu ala gln
AGG TAC TCC ATC CAG AAC GCC GCT GCC TTC TGC TTC TCC GAG ACC ATC CCG GCC CCC ACG GGC AAG GAC GAG GCC CAG
                        +750                                            +800 gln arg ser
CAG AGA TCG GTGAGTGGCCACTGCCAGCGGGAGCAGGGGCCTCCCTCTTCCTAAGAAGGCTGCCCCATCTTCATCATCAGGCCTTGGCCGGC
                      +800                                      +850 asp
CTTCTCCCCGAGCTGGTGGGGTGATGTGGCAGAGGGCGGGGCTGGTGAGGGCCACGGCCCCCATCCACGGCCATCTGCCCGCAG GAC
                  +900                                       +950                                  +1000 val glu leu leu arg phe ser leu leu ile gln ser trp leu gly pro val gln phe leu ser arg val phe thr asn
GTG GAG CTG CTG CGC TTC TCG CTG CTC ATC CAG TCG TGG CTC GGG CCC GTG CAG TTC CTC AGC AGG GTC TTC ACC AAC
                                          +1050 ser leu val phe gly thr ser asp arg val tyr glu lys leu lys asp leu glu gly ile gln ala leu met arg
AGC CTG GTG TTT GGC ACC TCA GAC CGC GTC TAC GAG AAG CTG AAG GAC CTG GAG GGC ATC CAG GCC CTG ATG CGG GT
                      +1100                                  +1150

GGGGAGGGCGGCTCGGGTCCCCACACTCGGCCTCTCTCCCGGCTGAGCGAAGCCGGTGGGGCTGGGGGAGAGGCTCCCATGCT
                                        +1200                                  +1250
```

Fig. 3c.

```
CTCTCTCTAGCAGTTCACTCTCCACCCCGACAAATCTTTCCCCATTTCCCCCTCGGAGTCTTCCCCTTTGTCTTCTTCAAGCATGGAGGGGAGGGTCGAAGAC
                                 +1300                                          +1350
                                                                     SmaI
                                                    glu leu glu asp gly ser pro arg ala gly gln
                                                    GAG CTC GAG GAT GGC AGC CCC CGG GCA GGA CAG
GGAGGGGACAGGAGAGCGCCGCTGCCAAGGACTCGGCCCTCTCTCTCTCTCCCCTTTTGCAG
                    +1400                                    +1500                          +1550
ile leu lys gln thr tyr asp lys phe asp thr asn leu arg ser asp asp ala leu leu lys asn tyr gly leu leu ser
ATC CTC AAG CAA ACC TAC GAC AAA TTT GAC ACA AAC TTG CGC AGT GAT GAC GCG CTG CTT AAG AAC TAC GGG CTG CTC TCC
                                      A
                                                                                                    +1600
cys phe lys lys asp leu his lys ala glu thr tyr leu arg val met lys cys arg arg phe val glu ser ser cys ala
TGC TTC AAG AAG GAC CTG CAC AAG GCT GAG ACA TAC CTG CGG GTC ATG AAG TGT CGC CGC TTC GTG GAG AGC AGC TGT GCC
phe ***                                                                       T
TTC TAG TTGCTGGGCATCTCTGTGCCCCTCCCCAGTACTCCCCTGCACCCTGGAAAGTGCCACCCCCATGCCTGCTGTCCTTTCCT AATAAA ACCAGGTTGC
              +1650                              +1700
     ATGTCTCAGTA GGTCTCACT CTCGGATGGAGGAGGTGGGGCACTACCCCAAGGGGTGGGGCTGCAAGACAACTCGCAGGCATCCTTGGGGTCTC
              +1750                                  +1800
CTGGGGACTAGACACTGAATGATGGTTGACCCGGCTTCTTCCTGGCTTGAAAGACCACGAGGCACATTACTTCTCTCTCTTACACACCCACTGCTCAG
                +1850                                        +1900
GTCTGCAGTCCAGCTTGCTCGGCACTCATAGGTCAGGACCACCCCCCATCCTGCTACACCCCCTCCCATAAAGTACCCA.AGAATGGAAAGAGATGAAAGCCAAG
                                  +2000                                                +2050
```

```
                    RBS
         +24
pKIGH    ...CACAGGAAACAGACC ATG GCT GCA GGC CCT CGG ACC TCC GTG CTC CTG...
                            met ala ala gly pro arg thr ser val leu leu pGHX.1   ...CACAGGAAACAGACC ATG TTC CCA GCC ATG CCC TTG TCC AGC CTA TTT...
                            met phe pro ala met pro leu ser ser leu phe pGHX2.1  ...CACAGGAAACAGACC ATG GAG GAT GAT TAA ATG TTC CCA GCC ATG CCC...
                            met glu asp asp *** met phe pro ala met pro pGHXF    ...CACAGGAAACAGACC ATG GAG GAT AAC GGT TTC CCA GCC ATG CCC...
                            met glu asp asn gly phe pro ala met pro pGHXS.4  ...CACAGGAGGTAATAT ATG TTC CCA GCC ATG CCC TTG TCC AGC CTA TTT...
                            met phe pro ala met pro leu ser ser leu phe pGHXS.9  ...CACAGGAGGTAAAAT ATG TTC CCA GCC ATG CCC TTG TCC AGC CTA TTT...
                            met phe pro ala met pro leu ser ser leu phe pGHXC.1  ...CACAGGAAACAGACC ATG TTC CCA GCC ATG CCG CTG TCC AGC CTG TTC...
                            met phe pro ala met pro leu ser ser leu phe pGHXSC.4 ...CACAGGAGGTAATAT ATG TTC CCA GCC ATG CCG CTG TCC AGC CTG TTC...
                            met phe pro ala met pro leu ser ser leu phe
```

A

B

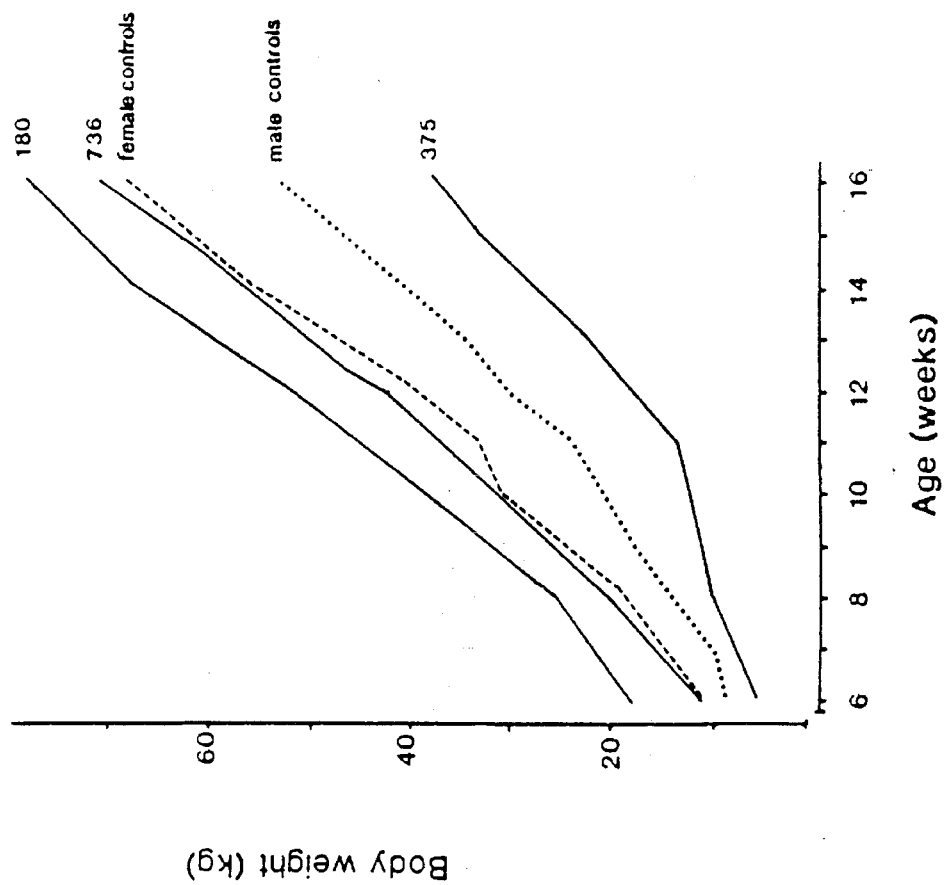
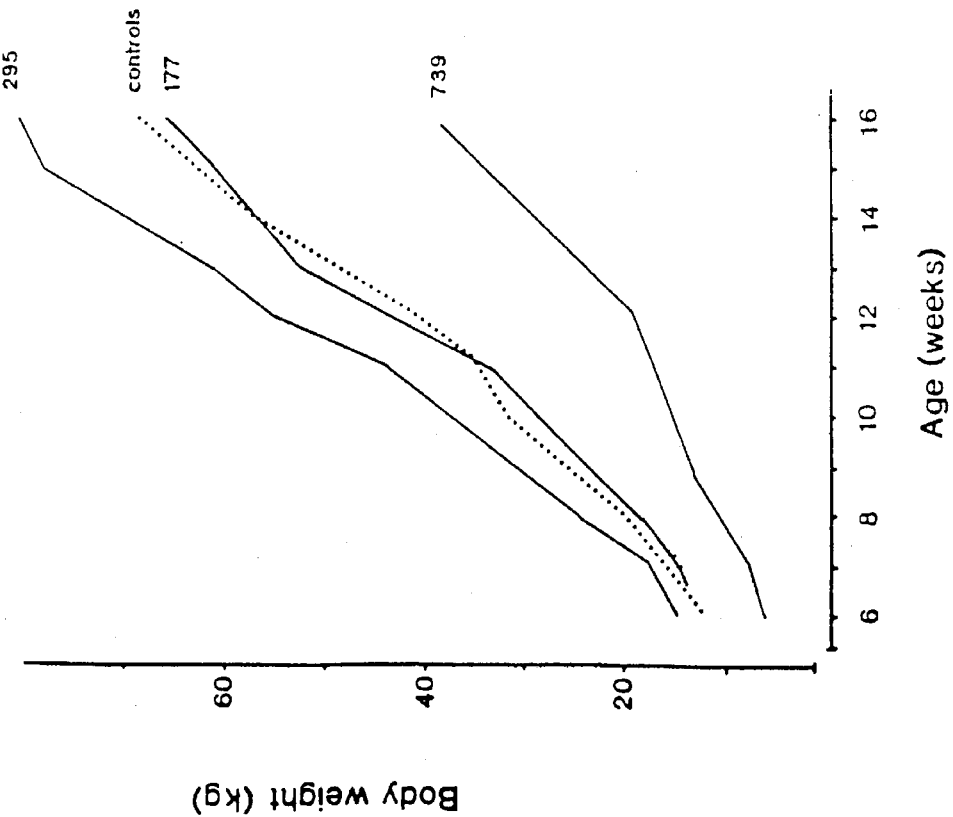
Fig.11.

– 5,573,933 –

TRANSGENIC PIGS

CROSS-REFERENCE TO RELATED APPLICATIONS

This is a continuation of application Ser. No. 07/808,194, filed Dec. 13, 1991, now abandoned which is a continuation-in-part application of Ser. No. 07/294,562 filed Dec. 14, 1988, now abandoned. application Ser. No. 07/294,562 was a national stage application based on PCT/AU88/00109, filed Apr. 14, 1988. The parent application claims priority from Australia PI1427, filed Apr. 14, 1987 and Australia PI5326, filed Nov. 10, 1987. Priority is claimed from the above recited applications, to the extent entitled.

FIELD OF THE INVENTION

This invention relates to animal husbandry and in particular to methods of creating new breeds of animals having desired characteristics, such as, increased weight gain, feed efficiency, milk production or disease resistance.

In traditional breeding processes it has been possible to achieve animals with particular desired characteristics. However, many unwanted, as well as the desired characteristics are often obtained in such processes.

Recently there has been major developments relating to the introduction of exogenous genes into the gene line of animals. In general, this is achieved by the use of both R/DNA technology (which includes isolation and characterization of a gene) and one-cell embryo techniques, including egg collection and re-implantation. In summary the overall method involves the following steps:

isolation of a pure gene sample (a fragment of DNA;

collection of a recently fertilized egg;

injection of a tiny portion (e.g. $10^{-9}$ of one cube centimeter) of the gene solution into the male nucleus (from the sperm) before it fuses with the female nucleus to form the one-cell embryo; and implanting the injected egg into a suitably prepared surrogate mother.

After the offspring is born, a small portion of tissue (usually the tail) is taken and DNA is prepared therefrom which can be assessed to establish whether the gene injected at the one-cell stage has been stably incorporated into the animal's chromosomes. If so, it is transgenic.

The process described above has been successfully used to accelerate growth and increase size in mice by the introduction of a gene construct incorporating exogenous genes, such as human growth hormone. However, the process has not been successful in attempts to enhance desired characteristics in farm animals.

It is an object of the present invention to overcome, or at least alleviate, one or more of the difficulties and/or deficiencies related to the prior art processes.

BRIEF DESCRIPTION OF THE DRAWINGS

FIG. 3A–3C illustrates the nucleotide sequence of the PGH genomic gene.

FIG. 4 illustrates a comparison of the sequence homology of the porcine (P), bovine (B), human (H), and rat (R) GH and the human placental lactogen (HPL) gene promoter and 5' untranslated sequence.

FIG. 6 illustrates the nucleotide sequence of the final 24 basis of the MRNA leader and the 5' end of the coding region of the PGH expression plasmids.

FIG. 11 illustrates the growth rate of transgenic pigs compared to the growth rate of non-transgenic littermates.

SUMMARY OF THE INVENTION

Figure 1:
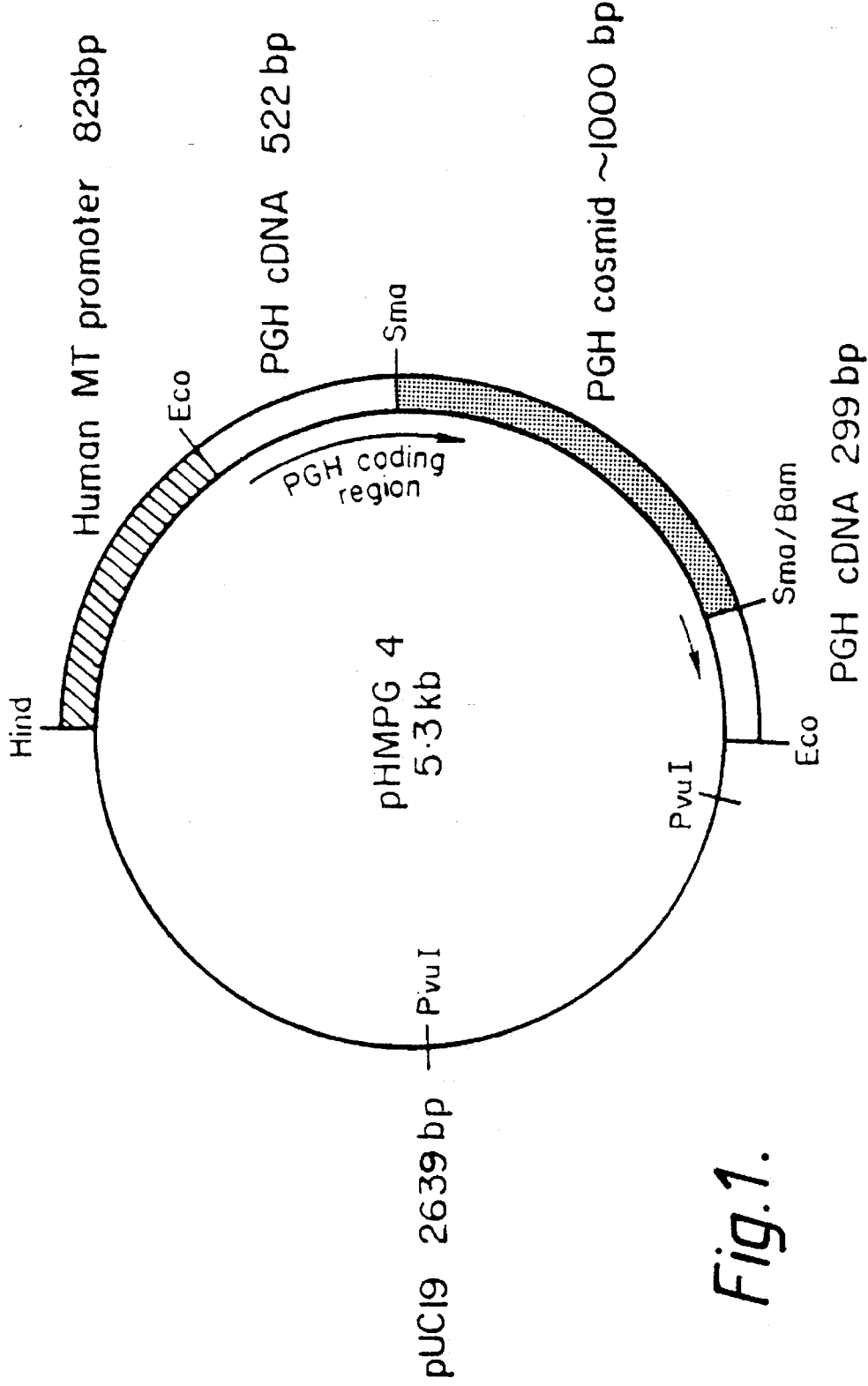
FIG. 1 is a diagram of the pHMPG.4 construct.

According to one aspect of the present invention there is provided a method for creating new breeds of animals which comprises:

(a) obtaining a recently fertilized ovum;

(b) isolating a gene sample of a characterizing hormone homologous with the ovum;

(c) introducing the gene sample into the male nucleus of the ovum prior to fusion with the female nucleus to form a single cell embryo; and, (d) subsequently implanting the ovum into a suitably prepared female animal.

The recently fertilized ovum may be of any suitable animal. Suitable animals include farm animals such as horses, cows, pigs, sheep, goats, turkeys and also marine animals such as abalone. The fertilized ovum may be obtained by any known method.

The gene sample of a characterizing hormone homologous with the ovum will necessarily be dependent upon the animal egg obtained. For example, if the animal egg obtained is of a pig then the gene sample will comprise characterizing pig hormones.

The type of characterizing hormones isolated and injected may be any desired characteristic hormones. The type of hormones isolated and injected may be dependent upon the desired characteristics of the off-spring. For example, if the off-spring is a porcine animal and the desired characteristic is accelerated growth, the gene sample may comprise porcine growth hormone. The gene sample may be isolated by any known method.

According to a further aspect of the present invention there is provided a plasmid expression vector including a first cloned sequence of DNA encoding a non-porcine promoter region and a second cloned sequence of DNA having porcine growth hormone (PGH) activity.

The plasmid expression vector so formed may include a complete copy of the porcine growth hormone in coding region.

Any suitable plasmid expression vector or cloning vector may be used. For example the plasmid cloning vector pUC19 (Nonander et al, 1983 Gene 26: 101–106) has been found to be suitable.

The first cloned sequence of DNA may encode a human promoter region. The human promoter region may be the human metallothioneine promoter (hMTIIA). In a preferred form, a modified metallothioneine promoter plasmid may be used.

The first cloned sequence of DNA may form an Eco RI-Hind III insertion in the plasmid cloning vector. This insertion may be approximately 810–823bp in length. In a preferred embodiment it is 823bp in length. The first cloned sequence of DNA may also contain elements of the human metallothioneine promoter.

The DNA sequence coding for porcine growth hormone activity may be isolated from a cDNA library formed from messenger or polyadenylated RNA. For example this may be isolated from porcine pituitary tissue.

The second cloned sequence of DNA may form an Eco RI-Eco RI insertion in the plasmid expression vector. This insertion may be approximately 522 bp in length. The plasmid is a small, high copy number expression vector. The plasmid expression vector may be plasmid pUC19 or pKT52.

The plasmid according to the present invention may further include a third cloned sequence of DNA. The third cloned sequence may include the 3' end of the porcine growth hormone gene. The third cloned fragment may form an Sma:Bam/Sma insertion in the second cloned fragment of DNA. This insertion may be approximately 1000 bp in length.

The 3' end fragment may also be modified. In one embodiment the certain regions identified as repeated sequences are deleted. For example the repeats may be deleted to leave approximately 200 base-pairs of 3' fragment as opposed to approximately 1000bp in the original sequence. The modifying of the 3' end of the porcine growth hormone DNA sample to remove repeated sequences is an additional contributing factor to stabilize chromosomal rearrangements of transgenes in the pig genome. This stabilization may also be achieved by including introns in the porcine gene coding region.

The repeated sequences may cause unfavorable rearrangements in transgenics. This problem is not encountered with growth hormone genes from other species. Removal of these repeats still showed that positive results could be obtained; this result being unforseen.

It has been found surprisingly that the inclusion of the 3' end fragment to the coding region may also provide added stability to the read-out sequence (the messenger RNA or mRNA) from the gene.

A particular plasmid of the type described above is that designated pH MPG.4, a sample of which is maintained in the culture collection of the University of Adelaide, Australia. Accordingly in a preferred aspect of the present invention, there is provided the plasmid pHMPG.4. A diagram of the pHMPG.4 construct is provided in FIG. 1.

There is also provided a plasmid wherein the repeated sequences are deleted to provide a plasmid which affords greater stability when incorporated into the DNA. Accordingly, there is provided a plasmid pHMPGΔ.5.

In a further aspect of the present invention there is provided a method of preparing a plasmid expression vector as described above which includes providing a suitable plasmid cloning vector, a first fragment of DNA containing a non-porcine promoter, and a second fragment of DNA coding for porcine growth hormone;

inserting the first fragment of DNA into the plasmid cloning vector at a suitable site; and inserting the second fragment of DNA into the plasmid cloning vector at a suitable site.

The method according to this aspect of the present invention may further include:

providing a third cloned fragment of DNA including the 3' end of the porcine growth hormone gene from the chromosomal copy of the porcine growth hormone gene.

This further step may be achieved by cleaving the restricted plasmid expression vector at a restriction site for the porcine growth hormone DNA portion and cloning the third fragment of DNA into the second fragment at a suitable site.

Figure 2:
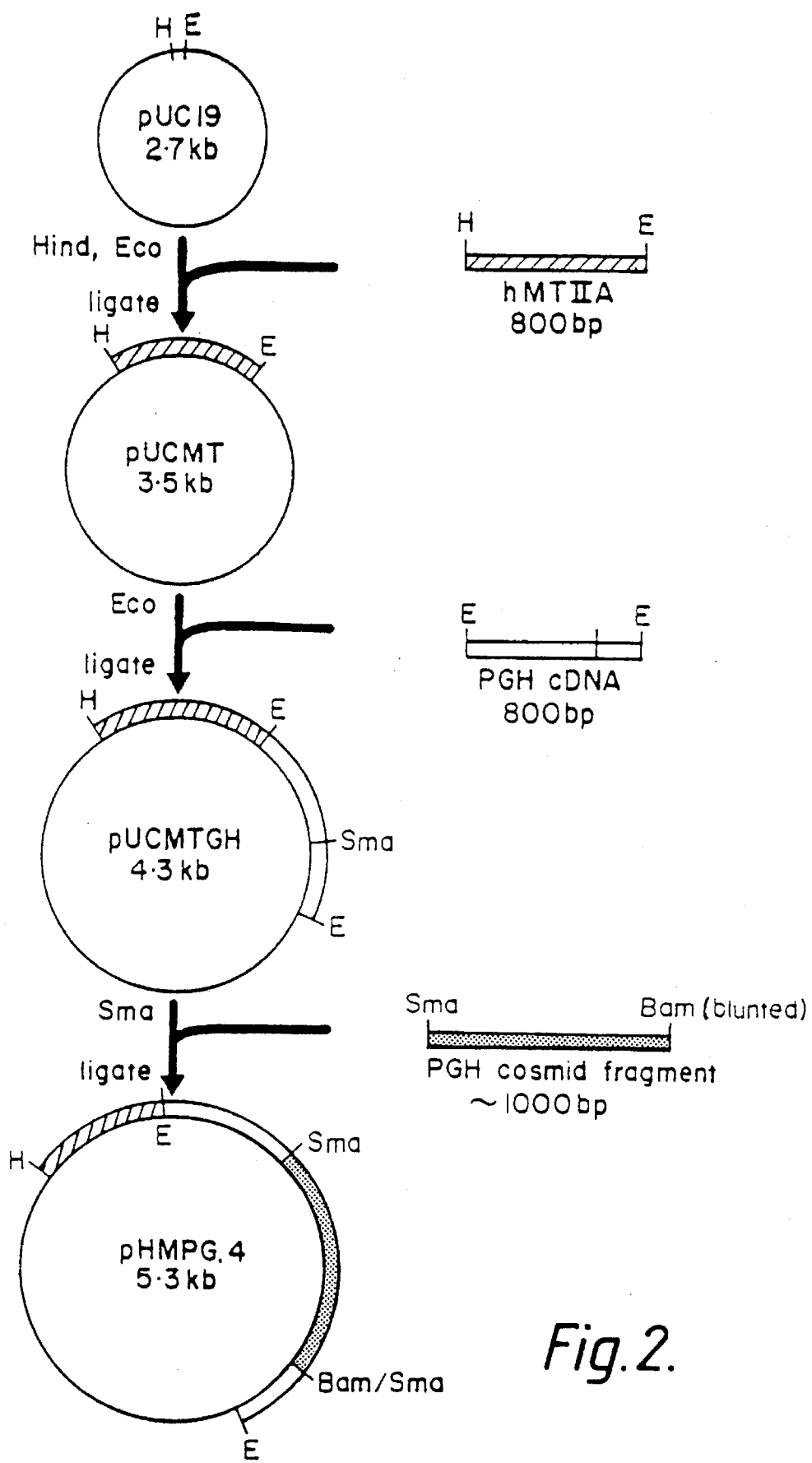
FIG. 2 is a diagrammatic summary of the construction of the pHMPG.4 plasmid.

These steps are summarized in FIG. 2.

It will be understood that the method of preparing a plasmid so described may include the preliminary step of characterizing the coding region and when relevant the 3' non-coding region of porcine growth hormone. This characterization of porcine growth hormone is described below. The nucleotide sequence of the PGH genomic gene is illustrated in FIG. 3.

The plasmid or gene sample, for example the porcine growth sample Hind III/PvuI segment derived from the plasmid shown in FIG. 1, may be introduced into the male pronucleus of an ovum of a porcine animal by any suitable method. The gene sample may be injected into the male pronucleus of the ovum.

In a preferred aspect of the present invention, there is provided a method of preparing a transgenic animal including:

(a) providing a recently fertilized ovum from a female of the animal;

(b) preparing a plasmid expression vector containing the first and second cloned fragments of the promoter and cloning regions of the gene to be expressed, and, (c) injecting the plasmid into the male pronucleus prior to fusion with the female nucleus to form a single cell embryo.

A major problem encountered with the injection of the gene construct into the male pronucleus is visualization of the pronuclei or nuclei in the ova. Nuclear structures of such animals as rabbits may be readily seen. However, pronuclei and nuclei in such animals as sheep and pigs are difficult to locate.

Pronuclei and nuclei of sheep ova may be seen by fluorescent microscopy using DNA specific fluorochromosomes or by interference contrast (IC) microscopy. The combination of stain and ultraviolet light may be damaging to the ovum. Therefore interference contrast microscopy is preferred for microinjection of sheep ova. Fluorescent analysis has indicated that interference contract microscopy is an effective method for pronuclear localization in approximately 80% of fertilized sheep ova. A similar process may be used to visualize pronuclei and nuclei of goat ova.

Pig ova are opaque and no nuclear structures can be seen even with interference contrast microscopy. However, the pronuclei or nuclei of pig ova may be visible if natural pig ova is centrifuged at 15000 g for 3 min. A similar process may also be used to visualize pronuclei and nuclei of cow ova. However, centrifugation does not help visualization of pronuclei of sheep ova.

The injection of the pronucleus may be carried out under magnification and use of standard microinjection apparatus. The ova may be held by a blunt holding pipette and the zona pellucida, plasma membrane and pronuclear envelope may be penetrated by an injection pipette. The blunt holding pipette may have a diameter of approximately 50 μm. The injection pipette may have a diameter of approximately 1.5 μm.

The amount of gene construct injected will necessarily be dependent upon the size of the pronucleus and the size of the injection pipette. For example, a few hundred copies of a 2.6 kilobase (kb) linea fragment containing the desired gene characteristic hormone may be injected.

The egg may be subsequently implanted by any suitable method into any suitably prepared surrogate mother. This may be achieved by any known method.

To further illustrate the invention the following non-limiting example is provided:

EXAMPLE 1

PGH cDNA Sequences

A porcine pituitary cDNA library of approximately 4000 individual recombinants constructed using the plasmid vector pUC19 (Norrander et al., Gene, 26, 101–106 1983) allowed the isolation of PGH cDNA clones using a synthetic DNA probe. One of the cDNA clones isolated, pPG.3, which was found to contain an insert of the expected full length, was completely sequenced.

The open reading frame of the pPG.3 cDNA insert was found to code for a 216 amino acid pre-hormone, identical in amino acid sequence to the partial length PGH cDNA clone of Seeburg et al. DNA, 2, 37–45 (1983). This clone provided for the first time the complete sequence of the region encoding the PGH signal sequence and 41 basis of the 5' untranslated region.

The nucleotide sequence within the coding region is very highly conserved, with only a single base difference from the sequence of Seeburg et al (1983).

FIG. 3

Nucleotide Sequence of the PGH Genomic Gene

The complete 2231 bp sequence is illustrated. The open reading frame which includes pre-PGH is indicated, as are bases which differ in sequence from the previously studied PGH cDNA sequence, pPG.3. Base changes which result in amino acid substitutions are marked with an asterisk. The single base in the 3' untranslated region which differs from pPG.3 is also indicated below the sequence. The location of the cap site (+1) was inferred from the position of the rat and human GH gene cap sites (Page 35 al., 1981; DeNoto et al., 1981).

Putative promoter and polyadenylation sequence, such as the TATA, AATAAA and GT-rich sequences are underlined, and the position at which the poly A tail is added is indicated with an arrow. The variant GC donor splice site is located in the first intron, around base +72.

The SmaI restriction site utilized for subcloning in latter Chapters is indicated.

Southern Analysis using a PGH cDNA Hybridization Probe

When the cDNA insert of pPG.3 was used to probe Southern blots of porcine genomic DNA digested with three different restriction enzymes, a single strongly hybridizing band was detected in each track. Enzymes BamHI and EcoRI also produced a second, fainter band, indicating that if the gene was in fact present as a single copy, the genomic gene must contain internal sites for both of these enzymes, somewhere near the end of the region homologous to the cDNA (as was later discovered to be correct). The third enzyme used, Hind III, produced only a single clear band. Taken together these data indicated that only a single copy of the GH gene exists in the porcine genome (per hapoid chromosome comlement), a situation analogous to the bovine and rat genomes, but very different to that of humans.

Isolation and Analysis of the Genomic PGH Gene

The PGH cDNA clone pPG.3 was used to screen a porcine cosmid library and isolate a clone containing PGH gene sequences (2.4). Southern analysis of the cosmid clone identified major BamHI and EcoRI hybridizing bands where were equal in size to those detected in genomic Southerns utilizing the same hybridization probe. Nucleotide sequencing of the gene contained within the cosmid revealed that the entire coding region was present (648 bp), along with 178 bp of the promoter region, 61 bp of 5' untranslated sequence, four introns of 242, 210, 197 and 278 bp respectively, and 414 bp of 3' non-coding sequence (FIG. 3). The gene contains four base alterations within the coding region relative to the previously sequenced PGH cDNA clone, pPG.3. The base substitutions, which are illustrated in FIG. 3, result in the alteration of two amino acid residues within the signal peptide. The remaining two differences are silent substitutions. There is also one base change in the 3' untranslated region relative to the pPG.3 cDNA sequence (FIG. 3).

The sequence comparison illustrated in FIG. 4 indicates that the promoters of each of the studied sequences share a high degree of homology. FIG. 3 indicates that the 5' untranslated regions of the GH and HPL genes are also conserved to a surprising degree.

Analysis of the 3' sequences of the PGH gene allowed the identification of sequences which have been shown to be important in the polyadenylation process.

The comparison of the 3' sequences of the PGH gene to all of the available GH and HPL sequences has revealed that these are also conserved to a surprising extent, between both GH and HPL genes.

FIG. 4

Comparison of GH and HPL Gene Promoter and 5' Untranslated Sequences

Porcine (P), bovine (B), human (H) and rat (R) GH genes and the human placental lactogen (HPL) gene were aligned to determine the extent of sequence homology (2.5.3). Asterisks indicate homology between adjacent sequences. The PGH sequence is numbered with respect to the distance from the cap site (+1).

This example describes the cloning of the porcine GH cDNA insert contained in pPG.3 into a bacterial expression vector.

Expression of PGH in E.coli

Figure 5:
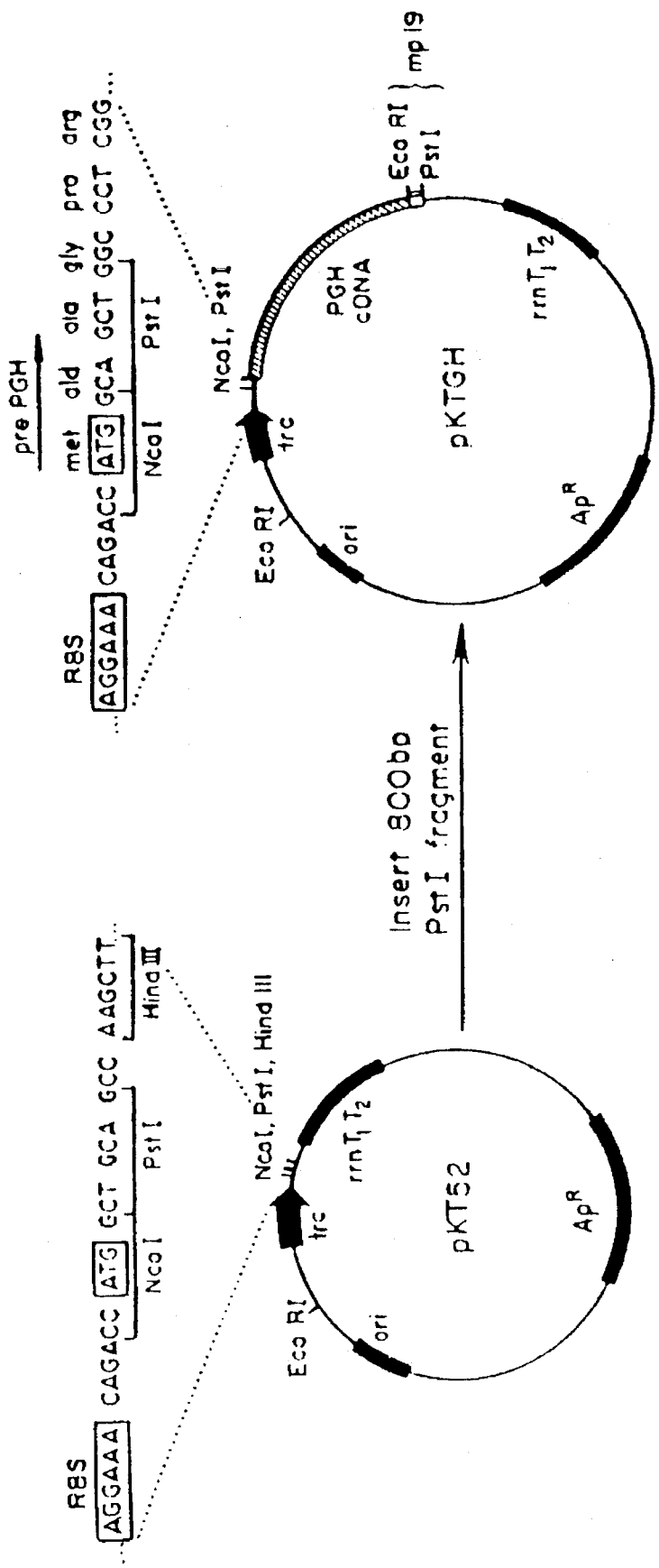
FIG. 5 illustrates the restriction map and sequence of the RBS/cloning region of pKT52 and cloning the PGH cDNA into expression vector pKT52.

The expression vector chosen for the production of PGH in E.coli cells was pKT52. This plasmid, kindly provided by J. Shine (California Biotechnology), is a small, high copy number expression vector which contains a powerful, regulatable trc promoter (Brosius et al., 1985) and the strong E.coli 5S transcription terminators (Brosius et al, 1981). The trc promoter is a fusion promoter containing the consensus −35 region of the E.coli trp promoter joined to the consensus −10 region of the E.coli lacUV5 promoter (do Boer et al., 1983a). The lacUV5 sequences of this promoter contain a lac operator site, which results in transcription from this promoter being repressed in lacI$^q$ strains. Transcription from this promoter in lac I$^q$ strains can be stimulated by growing cells in the presence of IPTG (de Boer et al., 1983a). A restriction map and the sequence of the RBS/cloning region of pKT52 is shown in FIG. 5.

FIG. 5

Cloning PGH cDNA into Expression Vector pKT52

The organization of the E.coli expression vector pKT52 is illustrated. An 800 bp PstI fragment was isolated from M13 RF containing the EcoRI insert of pPG.3. This fragment contained the entire pre-PGH coding region, minus the first two amino acids, plus 33 bp of mp19 polylinker DNA. When this fragment was inserted into the PstI site of pKT52, the full pre-PGH sequence is regenerated (3.2.1). The EcoRI insert of pKT52 was then isolated and cloned into M13 mp19 to facilitate mutagenesis of the pKT52/PGH cDNA junction point (3.2.2). The position of the trc promoter and the 5S rRNA transcription terminators (rrnT1 and rrnT2) are indicated.

Two E.coli strains were used for analysing expression levels in the work described in this Example, strains MC1061 and JM101. Expression from the trc promoter is constitutive in MC1061 cells, and repressed in the lac I$^q$ strain, JM101. The repression of transcription from the trc promoter in JM101 cells was released by growing cells in the presence of 1 mM IPTG.

Plasmid pGHX.1

A construct designed to express methionyl-PGH (m-PGH) was constructed using oligonucleotide directed mutagenesis to delete the DNA coding for amino acids 2–26 of the pre-hormone. This deletion joined the TTc codon of the first amino acid of the mature PGH molecule directly to the ATG initiator codon.

The EcoRI insert of pKTGH, which contains the entire PGH cDNA fused to the trc promoter sequences, was isolated and cloned into M13 mp19. Single-stranded DNA isolated from this phage was then used in mutagenesis reactions. To remove the 75 bases coding for amino acids 2–26 of the pre-hormone a 30 base long oligonucleotide, GH.30, complementary to 15 bases either side of the required deletion was used in a mutagenesis reaction. Following annealing and extension the mutagenesisreaction was transformed into JM101. The resulting plaques were then screened to detect the required deletion by plaque hybridization of duplicate lifts made from the transformation plates. Of the 150 plaques screened 35% were found to hybridize in duplicate to the GH.30 oligonucleotide probe. Single-stranded DNA was isolated from a number of positive plaques and sequenced to confirm the accuracy of the deletion using the PGH-specific oligonucleotide, GH.25, as primer. All the positive plaques contained DNA which had the correct deletion. Replicative form (RF) DNA was isolated from this deleted 'phage (mpGHX.1) and the EcoRI insert purified and subcloned into the larger EcoRI fragment of pKTGH to create plasmid pGHX.1. The nucleotide sequence of the 5' end of this, and the other expression plasmids described are illustrated in FIG. 6.

FIG. 6

Nucleotide Sequence of 5' Regions of PGH Expression Plasmids

The nucleotide sequence of the final 24 basis of the mRNA leader and the 5' end of the coding region of each of the expression plasmids generated in Chapter 3 are illustrated. Each of the sequences were determined by priming sequencing reactions with the PGH specific oligonucleotide, GH.25 (FIG. 5; 6.2.5). Each of the plasmids with the exception of pKTGH (pre-PGH) and pGHXE (PGH fusion protein) encode methionyl-pGH (m-PGH). Bases of the m-PGH expression plasmids which differ from the pGHX. 1 sequence have been underlined.

pGHXS (spacer) Plasmids

A 38 base oligonucleotide with one redundancy, GH.38, was designed to alter the RBS from AGGAAA to AGGAGG and the spacer from CAGACC to either TAATAT or TAAAAT. Single-stranded DNA containing the small EcoRI fragment of pGHX.1 was mutagenized and positive plaques selected and sequenced. A total of 30% of the plaques hybridized to the GH.38 probe, but of these only 20% contained either the GGTAATAT or GGTAAAAT RBS/spacer sequences. The remaining positives contained duplicate insertions which may have arisen due to the incorrect hybridization of the GH.38 oligonucleotide during the mutagenesis reaction. RF DNA was prepared from plaques containing correct versions of both the required alterations and then cloned back into pKTGH. The nucleotide sequence of the RBS/spacer region of the resulting plasmids, pGHXS.4 and pGHXS.9 are illustrated in FIG. 6. Extracts prepared from both MC1061 and induced JM101 cells containing either of these two plasmids were found to contain an additional prominent band, which had a molecular weight of 22K, the expected size of m-PGH. Laser densitometry of SDS/PAGE gels indicated that both plasmids produced identical levels of m-PGH, which ranged in the two hosts from 15 to 20% of total cellular protein.

Figure 7:
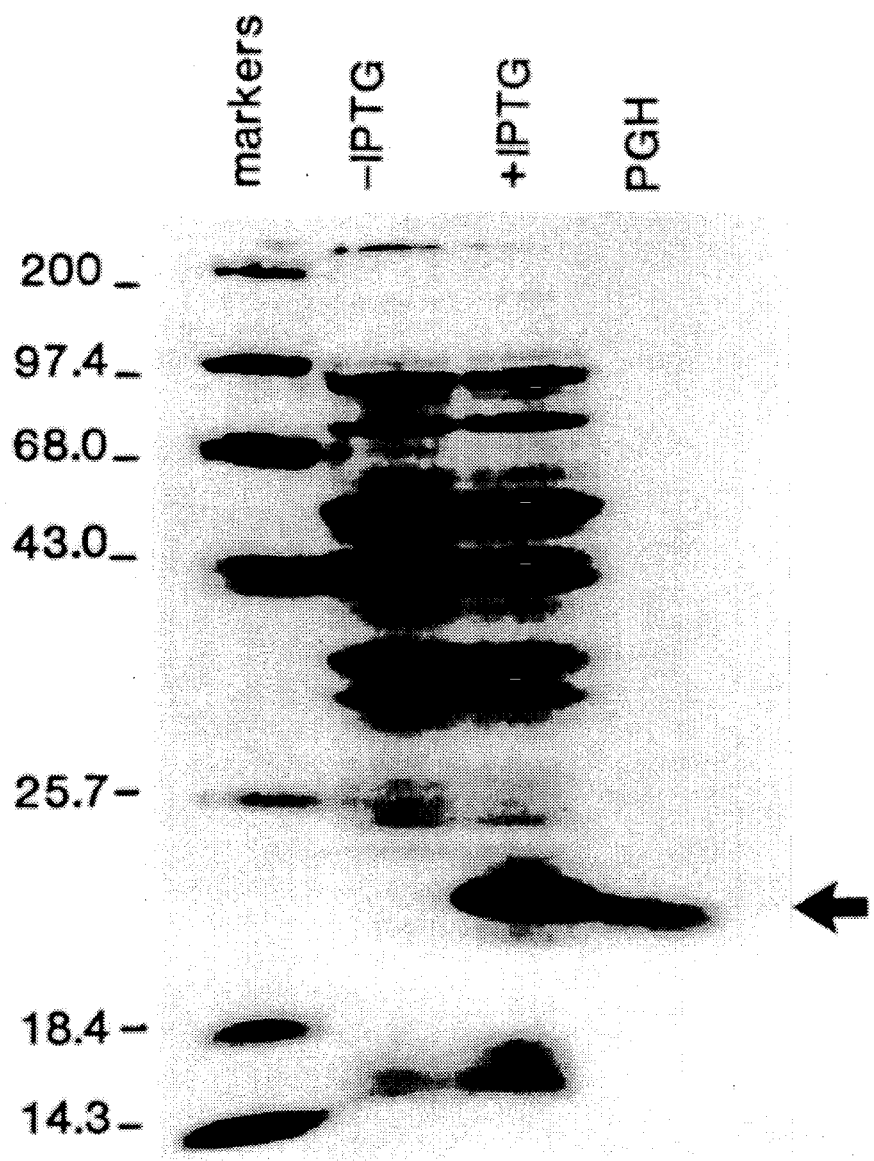
FIG. 7 illustrates the level of m-PGH produced from both uninduced and induced JM101 cells containing the pGHXS.4 expression plasmid.

FIG. 7 illustrates the level of m-PGH produced from pGHXS.4 in both uninduced and induced JM101 cells. This Figure also illustrates the similarity in molecular weight of the E.coli produced protein versus pituitary derived PGH. The m-PGH migrates at a slightly higher molecular weight than expected (approximately 200 daltons), probably due to the extremely crude nature of the protein extracts applied to the gel. This phenomenon has been previously observed in crude bacterial extracts containing human GH (Hsiung et al., 1986).

FIG. 7

Production of m-PGH by Plasmid pGHXS.4

Protein extracts from uninduced (–IPTG) and induced (+IPTG) JM101 cells containing expression plasmid pGHXS.4 were subjected to SDS/PAGE, along with molecular weight markets and purified, pituitary derived PGH (kindly provided by R. Seamark). A prominent band of the expected molecular weight of PGH (22,000 daltons) is produced only in IPTG induced cells (3.2.2.iii).

The Construction of a Human MT-IIA Promoter/PGH Fusion Gene

The promoter chosen for these studies was the human metallothioneine II-A promoter (Karin and Richards, 1982) which was kindly provided by R. Richards.

The hMT-IIA promoter was available as an 823 bp fragment with promoter sequences extending from –763 to +60 cloned in the M13 vector mp8 (A. Robbins pers. comm.). The double digestion of RF 'phage containing this promoter with HindIII and EcoRI releases the promoter sequences fused to 5 bp of vector polylinker sequence. This 823 bp fragment was purified and subcloned into HindIII/EcoRI digested pUC19 to generate plasmid pUCMT.

Figure 8:
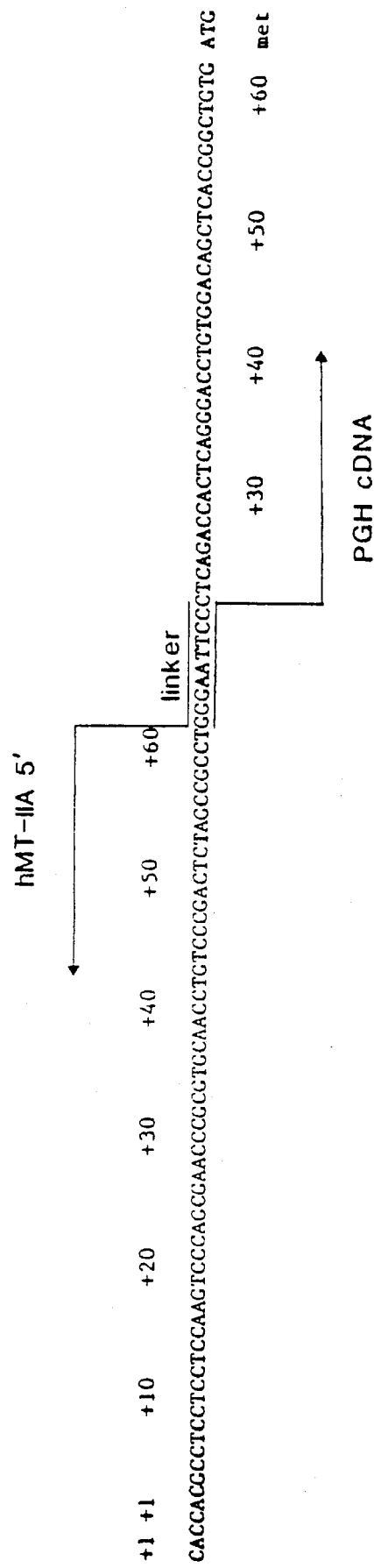
FIG. 8 illustrates the nucleotide sequence of the hMT-IIA and pGH junction point in pUCMTGH.4.

The sequences encoding PGH were isolated from the PGH cDNA clone pPG.3 as an 814 bp EcoRI fragment. This was cloned downstream of the hMT-IIA promoter, by restricting PUCMT with EcoRT, followed by ligation to the purified pPG.3 insert. Restriction analysis of plasmid DNA prepared from the resulting transformants (6.3.4.ii) identified a plasmid which contained the PGH cDNA inserted in the correct orientation, which was named pUCMTGH.4 (FIG. 2). The nucleotide sequence of the junction point between these two fragments was determined by the directional subcloning of a restriction fragment spanning this region into M13 mp18. The sequence data derived from this clone indicated that the expected sequence had been generated, and had contained the hMT-IIA promoter sequences and transcription start site (down to position +60) joined to the PGH 5' untranslated region (from +21 onwards) by 9 bp of polylinker/synthetic linker DNA (FIG. 8).

It was decided to subclone the 1 kb SmaI/BamHI fragment from plasmid pGHB.3 (2 kb BamHI subclone of cPGH.1) which contains the fifth exon downstream of the Sma I site plus approximately 800 bp of 3' non-translated sequence from the pgh gene into the unique SmaI site of pUCMTGH.4.

The 1 kb SmaI/BamHI fragment of pGHB.3. was purified (6.3.2.ii) and the BamHI generated overhang repaired with the Klenow fragment of E.coli DNA polymerase I. This blunt-ended fragment was then subcloned into SmaI digested pUCMTGH.4. The examination of plasmid DNA isolated from a number of the resulting transformants revealed that most were equal in size to pUCMTGH.4. The transformants were therefore screened for the presence of the cPGH.1 sequences by filter hybridization using a 500 bp BamHI/PstII restriction fragment from the far 3' end of pGHB.3 as the hybridization probe. Restriction analysis of plasmid DNA prepared from the resulting positives indicated that one contained the inserted fragment in the correct orientation. This plasmid was named pHMPH.4 (HM, human metallothionein; PG, porcine growth hormone). The organization of this plasmid is illustrated in FIG. 1.

To produce the modified plasmid pHMPGΔ.5, the 1 kb SmaI/BamHI fragment from plasmid pGHB.3 was purified and digested with Nuclease Bal31 prior to subcloning into SmaI digested pUCMTGH.4.

The tranformants were screened for the presence of the cPGH.1 sequences by filter hybridization using a 500 bp BamHI/PstI restriction fragment from the far 3' end of pGHB.3 as the hybridization probe. Analysis of the positives yielded a plasmid in the correct orientation which was named pHMPGΔ.5. This plasmid was used to create transgenic animals in the form of a plasmid or linear fragment.

FIG. 2

Construction of Eukaryotic Expression Plasmid pHMPG.4

A flow chart illustrating the construction of pHMPG.4 is illustrated. An approximate 800 bp HindIII/EcoRI fragment containing the hMT-IIA promoter was cloned into HindIII/EcoRi digested, dephosphorylated pUC19 to create plasmid pUCMT. This plasmid was then restricted with EcoRI, dephosphorylated, and ligated to the EcoRI insert of the PGH cDNA clone, pPG.3, to generate plasmid pUC-MTGH.4. This plasmid was restricted with SmaI, dephosphorylated, and ligated to the blunt-ended 1 kb SmaI/BamHI insert of cosmid subclone pGHB.3, which contains most of the last exon of the PGH genomic gene and approximately 700 bp of PGH 3' non-coding sequence to create pHMPG.4. All constructs were checked by DNA sequence analysis.

FIG. 8

Nucleotide Sequence of the hMT-IIA/PGH Junction Point in pUCMTGH.4

A ScaI/PstI fragment which covers the junction region between hMT-IIA and PGH cDNA sequences was isolated from pUCMTGH.4 and cloned into SmaI/PstI digested mp18 for sequence analysis. The sequence data from this clone indicated that the correct fusion had been generated, with the hMT-IIA promoter, cap site (there are two cap sites, both indicated as +1), and 5' untranslated sequences (extending down to +60), linked to the PGH cDNA sequences, which extend downstream from base +21, by 9 bp of synthetic linker sequence (4.2).

FIG. 1

Expression Vector, pHMPG.4

The restriction map and organization of expression vector pHMPG.4 is illustrated. The hMT-IIA promoter sequences are fused to a hybrid gene containing PGH cDNA sequences extending from +21 down to the unique SmaI site, joined to PGH genomic gene sequences downstream from this point. The 2.7 kb HindIII/PvuI fragment containing all of the promoter and PGH sequences, plus 120 bp of the pUC19 lacz gene joined to the 3' end, was purified from low melting temperature agarose, and used for generating transgenic animals.

Production of Transgenic Pigs

The HindIII/PvuI fragment of pHMPGΔ.5 was used to produce transgenic pigs. Single cell in vivo fertilized pig embryos were collected from superovulated large white sows. These were prepared and injected with approximately 600 copies of the pHMPGΔ.5 insert. Approximately 30 injected embryos were surgically transferred into the oviducts of each of a number of synchronized recipient sows. Four of these sows farrowed small litters (4–5 per litter), producing a total of 17 piglets.

Analysis of Transgenic Pigs i) Dot-blots

Figure 9:
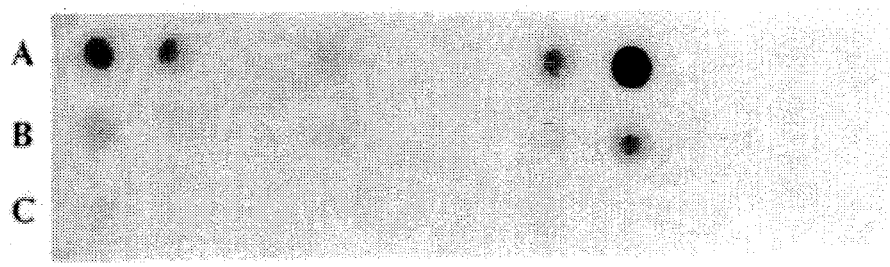
FIG. 9 illustrates the Dot-blot analysis of potentially transgenic pigs from the pHMPGΔ.5 insert.
Figure 9:
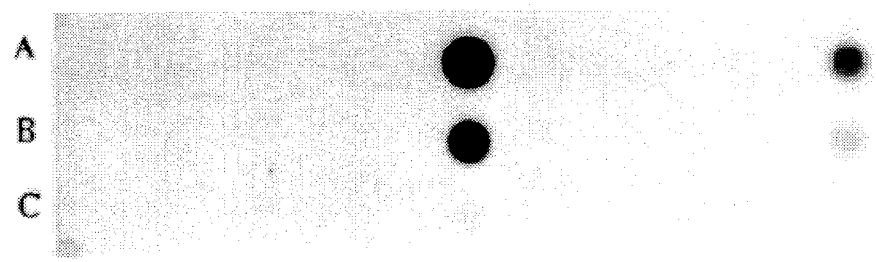
Figure 10:
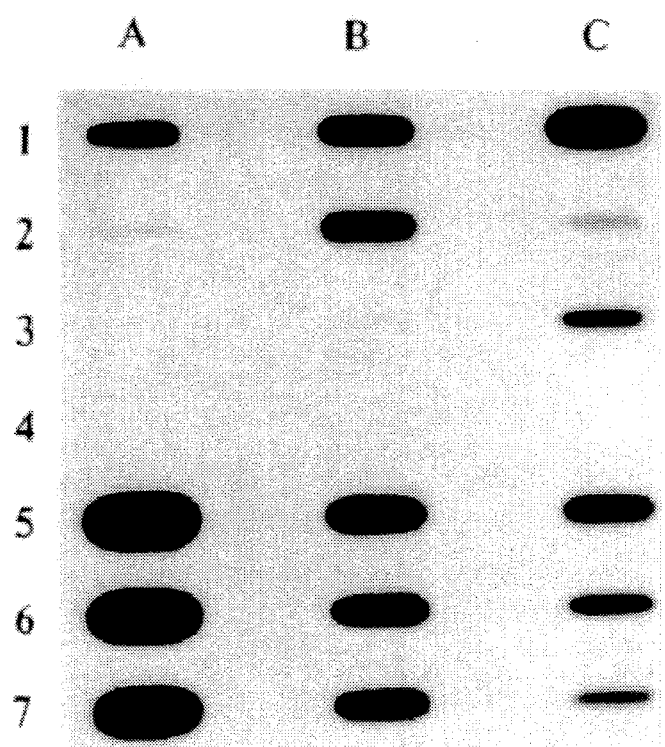
FIG. 10 illustrates the Slot-blot analysis of transgenic pig DNA containing various amounts of pHMPG.4 plasmid DNA with pig (PIG) and human (HUMAN) negative and positive controls.

The piglets were tested for the presence of the foreign gene by dot-blot hybridization of DNA isolated from tail tissue. Both normal pig DNA and human genomic DNA were included on these dot-blots to act as negative and positive controls respectively. Following the hybridization of these dot-=blots to the HindIII/AvaI fragment of the hMT-IIA promoter a number of positive signals were evident. Four of the pigs showed strong hybridization equivalent to greater than one copy per cell and a further two showed weak hybridization, slightly above background, and equivalent to less than one copy per cell (FIG. 9).

ii) Slot-blots

The number of copies per cell of the pHMPGΔ.5 insert present in each of the transgenic pigs was determined by slot-blot analysis. Five μg samples of tail DNA from each of the transgenic animals was filtered onto a slot-blot along with human and pig positive and negative controls. A range of amounts of pHMPGΔ.5 plasmid DNA (which also contained 5 μg of control pig genomic DNA) corresponding to genomic copy numbers equivalent to between one and fourty copies per cell were also included. This slot-blot was hybridized to the nick-translated HindIII/AvaI fragment of the hMT-IIA promoter and washed at high stringency. The intensity of hybridization of the transgenic animals was compared to the plasmid standard s by laser densitometry, and found to range from approximately 0.5 copies per cell in animals #375 and #739 to 15 copies per cell in animal #295 (Table 1; FIG. 9).

iii) Southern Analysis

The organization of the foreign sequences within the transgenic pigs was studied by Southern blotting. There are no BamHI sites within the pHMPGΔ.5 insert. The digestion of the genomic DNA of the transgenic animals with this enzyme should therefore produce bands on genomic Southerns, the length of which are governed by the distance of the nearest BamHI sites to the site of integration, the number of integration sites, and the number of integrated copies of the pHMPGΔ.5 insert.

FIG. 9

Analysis of Potentially Transgenic Pigs by Dot-blot 10, 5, and 1 μg samples of DNA isolated from the tails of pigs which had developed from eggs microinjected with the insert of pPLMPGΔ.5, were denatured and applied to a membrane. pHMPGΔ.5 and human (HUM) genomic DNA positive controls and pig (PIG) genomic DNA negative controls were included on each dot-blot array. The plasmid positive controls are in row 1, blot A. In this row the numbers in brackets refer to the number of copies per cell each plasmid dot is equivalent to. Samples in rows A4 to A11 and B1 to B9 contain the test pig samples. The nick-translated hMT-IIA promoter HinIII/AvaI insert was used as the hybridization probe. A key indicating the identity of the sample on each dot is shown below.

hybridization of each of the samples on this membrane was performed using a laser densitometer. The results of this analysis are presented in Table below.

|    | A        | B        | C        |
|----|----------|----------|----------|
| 1. | 177      | 180      | 295      |
| 2. | 375      | 736      | 739      |
| 3. |          | PIG      | HUM      |
| 4. |          |          |          |
| 5. | 500 (40) | 125 (10) | 50 (4)   |
| 6. | 375 (30) | 100 (8)  | 25 (2)   |
| 7. | 250 (20) | 75 (6)   | 12.5 (1) |

Table 1

Transgenic Pigs: Gene Copy Number, Growth, and Serum PGH Concentration

The number of copies (per cell) of the foreign gene present in each of the transgenic pigs estimated by slot-blot analysis, the daily weight gain (between days 50 and 120) and the serum PGH concentration of each of the transgenic pigs and their non-transgenic littermates are illustrated. The female control values are the mean of three animals, and the male control values are the mean of two animals.

| Pig No.  | sex | copy no./ cell | daily weight gain (gm) | serum PGH conc. (ng/ml) |
|----------|-----|----------------|------------------------|--------------------------|
| 177      | F   | 3              | 765                    | 10.4                     |
| 295      | F   | 15             | 953                    | 27.8                     |
| 739      | F   | 0.5            | 686                    | 6.9                      |
| controls | F   | —              | 806                    | 10.6                     |
| 180      | M   | 6              | 851                    | 15.3                     |
| 375      | M   | 0.5            | 487                    | 6.3                      |
| 736      | M   | 6              | 857                    | 11.1                     |
| controls | M   | —              | 670                    | 15.3                     |

|    |       |       | 1   | 2   | 3   | 4   | 5   | 6   | 7   | 8   | 9   | 10  | 11  |
|----|-------|-------|-----|-----|-----|-----|-----|-----|-----|-----|-----|-----|-----|
|    |       |       |     |     |     |     | A.  |     |     |     |     |     |     |
| A. | 10 μg | (2)   | HUM | PIG | 177 | 178 | 179 | 180 | 295 | 296 | 297 | 298 |     |
| B. | 5 μg  | (1)   | "   | "   | "   | "   | "   | "   | "   | "   | "   | "   |     |
| C. | 1 μg  | (0.5) | "   | "   | "   | "   | "   | "   | "   | "   | "   | "   |     |
|    |       |       |     |     |     |     | B.  |     |     |     |     |     |     |
| A. | 10 μg | 373   | 374 | 375 | 376 | 735 | 736 | 737 | 738 | 739 | PIG | HUM |     |
| B. | 5 μg  | (1)   | "   | "   | "   | "   | "   | "   | "   | "   | "   | "   |     |
| C. | 1 μg  | (0.5) | "   | "   | "   | "   | "   | "   | "   | "   | "   | "   |     |

FIG. 10

Slot-blot Analysis of Transgenic Pigs

Samples (5 μg) of transgenic pig DNA and pig (PIG) and human (HUM) negative and positive controls were denatured and applied to a membrane along with a number of samples containing various amounts of pHMPG.4 plasmid DNA combined with 5 μg of pig control DNA. The amounts of pHMPG.4 DNA applied correspond to gene copy numbers of between 1 and 40 gene copies per cell (shown in brackets below). The probe used was the nick-translated hMT-IIA promoter HindIII/AvaI insert. A key to the samples on the blot is given below. Quantitation of the intensity of Each transgenic animal is unique and the level of expression from incorporated transgenes is highly variable from one line to another. Such variation is common and it represents no problem. The transgenic animals are bred from an animal where insertion and expression have occurred as desired, as in Pig. No. 295.

FIG. 11

Growth Rate of Transgenic Pigs

The growth performance of each of the transgenic pigs is pitted against the growth rate of non-transgenic littermates. The dotted lines represent the average growth rate of sexmatched non-transgenic littermates, the dashed line represents the average of non-transgenic littermates of the opposite sex, and solid lines represent transgenic animals.

Example 2

Sp1 Binding Site Minus hMT-IIA/PGH Plasmid, pHMGPG.3

It has been reported that a consensus Sp1 binding site sequence, GGGcGG (Kadonaga et al., Trends Biochem. Sci. 11, 20–23, 1986) located adjacent to the basal level sequence, would generate a promoter with the desired parameters. The nucleotide sequence of an altered hMT-IIA promoter which has the Sp1 binding site replaced with a PstI linker, and possesses the required transcriptional characteristics, was kindly made available by M. Karin. This alteration was recreated in the hMT-IIA/mp8 clone by oligonucleotide directed mutagenesis.

A 46 base long oligonucleotide, MT.46 was designed to replace a 15 bp region, surrounding and including the Sp1 binding site, with a 17 base long PstI linker sequence. Following mutagenesis of hMT-IIA/mp8 single-stranded DNA with MT.46 and transformation into JM101 plaques containing the correct sequence substitution were selected by plaque hybridization and nucleotide sequencing. RF DNA was isolated from one of the plaques containing the correct mutation and the HindIII/EcoRI insert of pHMPG.4 and HindIII/EcRI digested pUC19 DNA. One of the resulting plasmids from this ligation contained the correct restriction pattern, and was named pHMGPG.3 (GC sequence minus).

The insert of this plasmid is currently being introduced into transgenic mice.

It is also envisaged that the process of the present invention may be used to produce synthetic promoter constructs containing various combinations of metal-responsive elements corresponding to sequences found in mouse, sheep or human metallothioneine promoters, with or without other promoter elements. For example it may be used to regulate $Fe^{++}$ levels.

Finally, it is to be understood that various other modifications and/or alterations ma be made without departing from the spirit of the present invention as outlined herein.

What is claimed and desired to be secured for Letters Patent is as follows:

1. A method for preparing a transgenic pig which overexpresses porcine growth hormone transgenic pigs, said method comprising the steps of:

(a) obtaining a recently fertilized pig ovum;

(b) isolating a first DNA sequence encoding a human metalliothionine IIA promoter;

(c) inserting the first DNA sequence into a plasmid cloning vector;

(d) isolating a second DNA sequence encoding porcine growth hormone, said second DNA sequence being an EcoRI fragment of approximately 814 base pairs;

(e) inserting the second DNA sequence into the plasmid cloning vector at suitable site such that the first DNA sequence can act as a promoter for expression of the second DNA sequence upon transgenesis;

(f) isolating a third DNA sequence including the 3' end of the porcine growth hormone gene, said DNA sequence including a SmaI/BamHI fragment of approximately 1000 base pairs;

(g) modifying the 3' end of the third DNA sequence by treatment with Bal31 to delete regions identified as repeated sequences;

(h) inserting the modified third DNA sequence into a SmaI site in the second DNA sequence to generate a plasmid expression vector;

(i) introducing the plasmid expression vector or a linerized insert therefrom comprising the first, second and third DNA sequences into the male pronucleus of said fertilized pig ovum prior to fusion with the female nucleus to form a single cell embryo; and, (j) subsequently implanting the ovum into a female pig and allowing the embryo, resulting from introduction of the plasmid cloning vector into the ovum, to develop to maturity.

2. A method according to claim 1 wherein the plasmid cloning vector comprises pUC19.

3. A method according to claim 1 wherein the first sequence of DNA forms an EcoRi-HindIII insertion in the plasmid expression vector and is approximately 810–823 base pairs in length.

4. A method according to claim 1 wherein the modified third DNA sequence is approximately 200 base pairs in length.

5. A method according to claim 1 wherein the plasmid expression vector is pHMPGΔ.5.

6. A plasmid expression vector comprising:

(a) a plasmid cloning vector;

(b) a first cloned sequence of DNA enclosing a human metalliothionine IIA promoter;

(c) a second DNA sequence encoding porcine growth hormone, said second DNA sequence being an EcoRI fragment of approximately 814 base pairs; and (d) a third DNA sequence including the 3' end of the porcine growth hormone gene, said DNA sequence including a SmaI/BamHI fragment of approximately 1000 base pairs which is modified at the 3' end thereof by treatment with Bal31 to delete regions identified as repeated sequences;

wherein said first DNA sequence can act as a promoter for expression of said second and third DNA sequences upon transgenesis; and wherein said third DNA sequence is inserted into a SmaI site in said second DNA sequence.

7. A plasmid expression vector according to claim 6 wherein the plasmid cloning vector comprises pUC19.

8. A plasmid expression vector according to claim 6 wherein the first cloned sequence of DNA forms an EcoRI-HindIII insertion in the plasmid expression vector and is approximately 810–823 bp in length.

9. A plasmid expression vector according to claim 6 wherein the modified third DNA sequence is approximately 200 bp in length.

10. A plasmid expression vector according to claim 6 which is pHMPGΔ.5.

11. A DNA fragment comprising:

(a) a first DNA sequence encoding a human metalliothionine IIA promoter;

(b) a second DNA sequence encoding porcine growth hormone, said second DNA sequence being an EcoRI fragment of approximately 814 base pairs; and (c) a third DNA sequence including the 3' end of the porcine growth hormone gene, said DNA sequence including a SmaI/BamHI fragment of approximately 1000 base pairs which is modified at the 3' end thereof by treatment with Bal31 to delete regions identified as repeated sequences;

wherein said first DNA sequence can act as a promoter for expression of said second and third DNA sequences upon transgenesis; and wherein said third DNA sequence is inserted into a SmaI site in said second DNA sequence.

12. A DNA fragment according to claim 11 wherein the first DNA sequence is an EcoRI-HindIII fragment of approximately 810–823 bp in length.

13. A DNA fragment according to claim 11 wherein the modified third DNA sequence is approximately 200 bp in length.

14. A DNA fragment according to claim 11 from plasmid expression vector pHMPGΔ.5.

* * * * *

UNITED STATES PATENT AND TRADEMARK OFFICE
CERTIFICATE OF CORRECTION

PATENT NO. : 5,573,933
DATED : November 12, 1996
INVENTOR(S) : Robert F. Seamark, et al.

It is certified that error appears in the above-indentified patent and that said Letters Patent is hereby corrected as shown below:

Col. 7, Line 40: "phage" should read --'phage--

Col. 9, Line 24: "Sma I" should read --SmaI--

Col. 11, Line 5: "fourty" should read --forty--

Col. 11, Line 29: "pPLMPG∆.5" should read --pHMPG .5--

Col. 13, Line 44: "ma" should read --may--

Col. 13, Line 49: delete "transgenic pigs" after the word "hormone"

Signed and Sealed this

Eighteenth Day of November 1997

Attest:

BRUCE LEHMAN

*Attesting Officer*    *Commissioner of Patents and Trademarks*